United States Patent [19]

Smith et al.

[11] Patent Number: 5,398,483

[45] Date of Patent: Mar. 21, 1995

[54] METHOD AND APPARATUS FOR PACKAGING, MIXING AND DELIVERING BONE CEMENT

[75] Inventors: Daniel B. Smith, Warsaw; Ronald L. Gilbert, Fort Wayne, both of Ind.

[73] Assignee: Polymers Reconstructive A/S, Farum, Denmark

[21] Appl. No.: 11,339

[22] Filed: Jan. 29, 1993

[51] Int. Cl.⁶ .................. B65B 29/10; A61F 1/00
[52] U.S. Cl. ......................... 53/474; 53/237; 53/433; 53/469; 206/219
[58] Field of Search ............ 53/474, 239, 238, 237, 53/473, 240, 469, 467, 433, 434, 432, 511, 512, 510; 206/219; 604/87, 89

[56] References Cited

U.S. PATENT DOCUMENTS

| | | | |
|---|---|---|---|
| 2,605,896 | 8/1952 | Rohdin | 206/219 |
| 2,690,179 | 9/1954 | Fox | 604/87 |
| 2,756,875 | 7/1956 | Yochim | 206/219 |
| 2,874,830 | 2/1959 | Birmingham | 206/47 |
| 2,893,547 | 7/1959 | Earl et al. | 206/219 |
| 2,932,385 | 4/1960 | Bollmeier et al. | 206/219 |
| 2,971,851 | 2/1961 | Kurtz | 203/219 X |
| 3,028,000 | 4/1962 | Clements et al. | 206/219 |
| 3,156,352 | 11/1964 | Hayhurst | 206/219 |
| 3,294,227 | 12/1966 | Schneider et al. | 206/219 |
| 3,462,070 | 8/1969 | Corella | 206/219 |
| 3,608,709 | 9/1971 | Pike | 206/219 |
| 3,618,283 | 11/1971 | Moore et al. | 53/474 X |
| 3,802,867 | 3/1973 | Gelpey | 206/47 |
| 3,802,919 | 4/1974 | Saffir | 53/474 X |
| 3,809,224 | 5/1974 | Greenwood | 206/219 |
| 3,847,279 | 11/1974 | Montgomery | 206/219 |
| 3,964,604 | 6/1976 | Prenntzell | 206/219 |
| 3,983,994 | 10/1976 | Wyslotsky | 206/219 |
| 4,000,996 | 1/1977 | Jordan | 206/219 X |
| 4,023,675 | 5/1977 | Claasen | 206/219 |
| 4,039,076 | 8/1977 | Desaules | 206/219 |
| 4,277,184 | 7/1981 | Solomon | 366/150 |
| 4,401,214 | 8/1983 | Kleckers | 206/219 |
| 4,402,402 | 9/1983 | Pike | 206/219 |
| 4,458,811 | 7/1984 | Wilkinson | 209/219 |
| 4,462,224 | 7/1984 | Dunshee et al. | 206/219 X |
| 4,463,875 | 8/1984 | Tepic | 222/82 |
| 4,608,043 | 8/1986 | Larkin | 206/219 X |
| 4,632,244 | 12/1986 | Landau | 53/474 X |
| 4,664,257 | 5/1987 | Nilson | 206/219 |
| 4,721,390 | 1/1988 | Lidgren | 366/139 |
| 4,795,265 | 1/1989 | Dahlberg et al. | 366/69 |
| 4,798,288 | 1/1989 | Holzner | 206/222 |
| 4,811,549 | 3/1989 | Usami et al. | 53/474 X |
| 4,910,259 | 3/1990 | Kindt-Larsen et al. | 525/259 |
| 4,927,012 | 5/1990 | Rowe | 206/219 |
| 4,952,068 | 8/1990 | Flint | 366/337 |
| 4,961,495 | 10/1990 | Yoshida et al. | 206/219 |
| 4,973,168 | 11/1990 | Chan | 206/219 X |
| 4,994,056 | 2/1991 | Ikeda | 604/87 X |
| 5,069,773 | 12/1991 | Frangioni | 206/219 X |
| 5,114,240 | 5/1992 | Kindt-Larsen et al. | 366/129 |
| 5,121,302 | 6/1992 | Bay et al. | 206/219 X |

FOREIGN PATENT DOCUMENTS

| | | | |
|---|---|---|---|
| 1054170 | 2/1954 | France | 206/219 |
| 1258379 | 3/1961 | France | 206/219 |
| 697723 | 9/1953 | United Kingdom . | |
| WO84/03830 | 4/1984 | WIPO . | |
| WO8606618 | 11/1986 | WIPO . | |
| WO90/13355 | 11/1990 | WIPO . | |

*Primary Examiner*—James F. Coan
*Attorney, Agent, or Firm*—Harness, Dickey & Pierce

[57] ABSTRACT

A method and apparatus for packaging, mixing and delivering bone cement. The apparatus may include a bone cement gun having a flexible container which is able to store at least two components of the bone cement. In this regard, the flexible container includes a first compartment that is able to store one component of the bone cement as well as a second compartment that is able to store the second component of the bone cement. A sealing member temporarily seals the first compartment with the second compartment, the removal of which permits the first and second components to be mixed so as to form the bone cement.

26 Claims, 5 Drawing Sheets

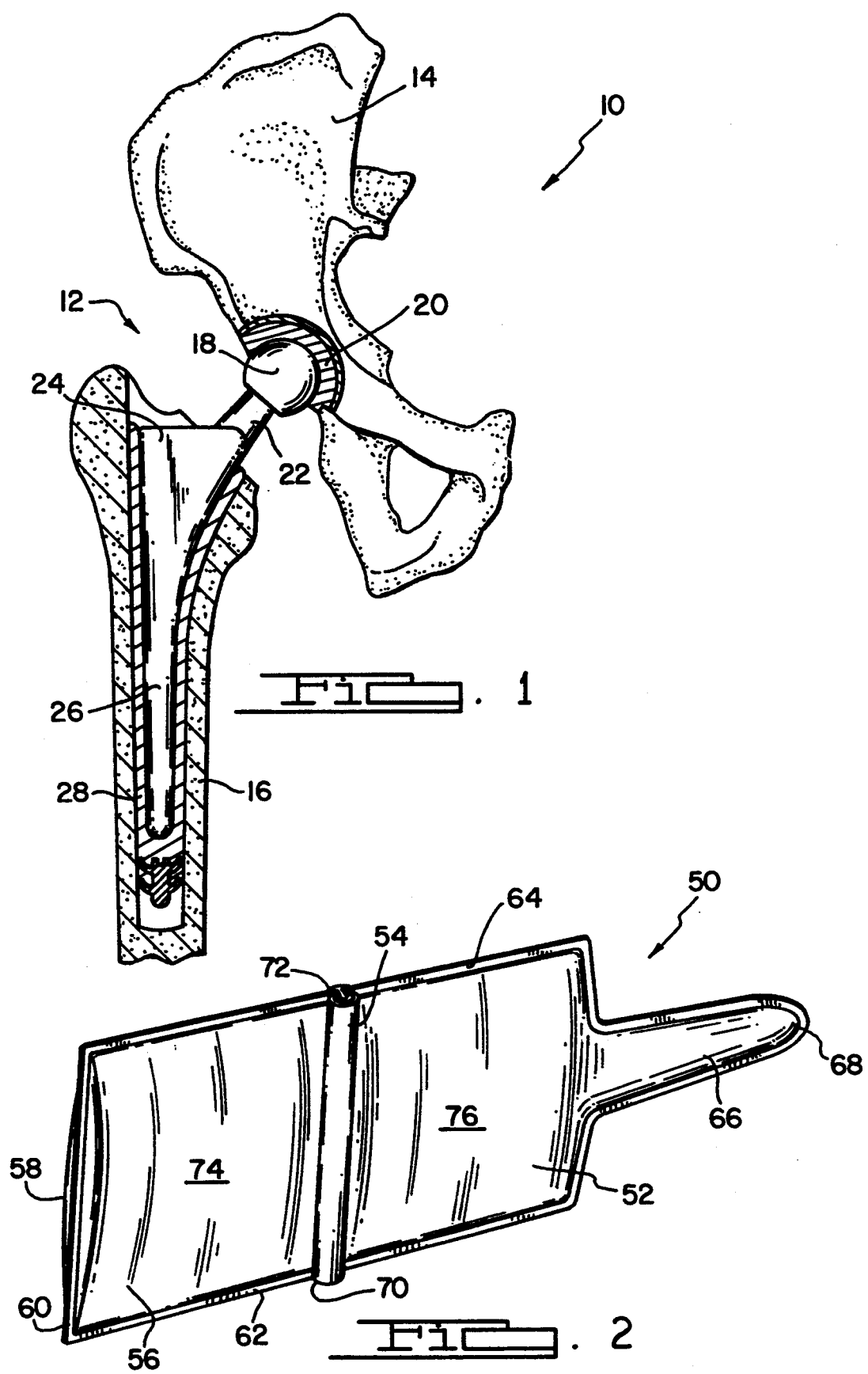

METHOD AND APPARATUS FOR PACKAGING, MIXING AND DELIVERING BONE CEMENT

BACKGROUND OF THE INVENTION

The present invention is directed toward a method and apparatus for packaging, mixing and delivering bone cement. More particularly, the present invention relates to a method and apparatus for intimately mixing the two or more components of bone cement wherein the components are initially kept in separate compartments of a flexible package.

The natural joints of the human body often undergo degenerative changes due to various etiologies. When these degenerative changes are advanced, irreversible and unresponsive to non-operative management, it may ultimately become necessary to replace the natural joint with a prosthetic device. When such replacement becomes necessary, the prosthetic device which is implanted is often secured to the natural bone by using bone cement.

Bone cement which is used to secure prosthetic devices to bone is comprised of a liquid monomer component that polymerizes about a polymeric powder component. In this regard, bone cement is generally formed from a methylmethacrylate monomer and polymethylmethacrylate or methylmethacrylatestyrene copolymer. The preparation of bone cement generally involves mixing the components in a suitable reaction vessel to form the bone cement. Generally, it is necessary that the components of bone cement be uniformly and thoroughly mixed so that a homogenous product is obtained.

During preparation of bone cement, various vapors are generated which are comprised primarily of the volatilized components of the bone cement. Because of the offensive smell such vapors may have, several evacuation and containment devices have been developed to minimize exposure to such vapors. Despite the advances in fume evacuation and containment during mixing, there has been little advancement in the art of packaging the bone cement to further minimize exposure to the offensive vapors.

Traditional open bowl bone cement preparation may, under certain circumstances, result in porosity in the bone cement product. Several vacuum mixing and centrifugation devices have been developed to minimize this porosity. While effective in the laboratory setting, these devices are complex and difficult to use which results in a variety of cement porosities achieved in the clinical setting. Furthermore, these systems are expensive and create a considerable quantity of disposable waste.

Accordingly, a need exists for a simple and inexpensive bone cement packaging system which will allow mixing of the two or more components while avoiding the above-mentioned disadvantages.

SUMMARY OF THE INVENTION

The present invention provides a flexible packaging system for bone cement which has both of the components of the bone cement supplied in a flexible package having two separate compartments. When preparing to use the bone cement, a member of the surgical staff removes a temporary seal separating the two compartments and then mixes the two components together by manipulating the flexible package. The bone cement can then be inserted into a bone cement gun having a reusable syringe and a disposable nozzle. Accordingly, the components of the bone cement gun and syringe remain relatively free of bone cement during the bone cement application.

An advantage of the present invention is to provide a packaging system for bone cement that minimizes the exposure to vapors which are generated during the mixing operation.

Another advantage of the present invention is to provide a packaging system for bone cement that reduces the amount of air mixed into the bone cement that would otherwise occur during traditional cement preparation, thereby reducing the porosity present in the cured bone cement.

Another advantage of the present invention is to provide a packaging system that is adaptable to be placed within a bone cement gun and that minimizes the number of components of the bone cement gun that must be cleaned or replaced due to contact with the bone cement.

A further advantage of the present invention is to provide a packaging system for bone cement that is relatively low in cost and relatively easy to use.

BRIEF DESCRIPTION OF THE DRAWINGS

Additional advantages of the present invention will become apparent from the following description and appended claims, taken in conjunction with the accompanying drawings in which:

FIG. 1 is an elevational view of a hip joint prosthesis shown in operative association with a hip and a pelvis;

FIG. 2 is a perspective view of the packaging system for bone cement which is used during the implantation of the hip joint prosthesis shown in FIG. 1 according to the preferred embodiment of the present invention;

DESCRIPTION OF THE PREFERRED EMBODIMENTS

Figure 3:
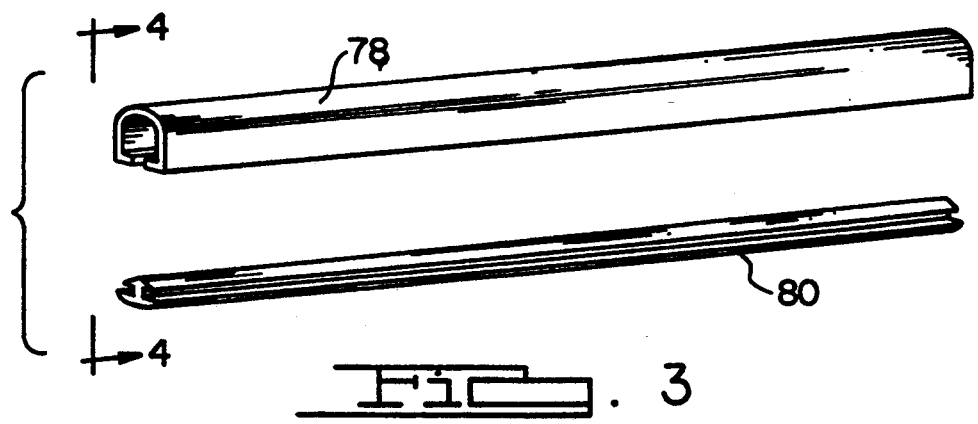
FIG. 3 is a perspective view of the temporary sealing device according to the preferred embodiment of the present invention.

The following discussion of the preferred embodiments of the present invention is merely exemplary in nature and is in no way intended to limit the invention of its application or uses.

Referring now to the drawings in which like reference numerals designate like or corresponding parts throughout the several views, there is shown in FIG. 1 a joint within the human body which is designated generally as reference numeral 10. The joint 10 includes a hip joint prosthesis 12 which is used for transferring a load between the pelvis 14 and a host femur 16. The hip joint prosthesis 12 is used to replace a natural hip after the natural hip has degenerated. While the following discussion will describe the use of the present invention in the context of a hip joint prosthesis, it will be understood that the present invention may also be applicable to other types of prosthetic components including the femoral component for a knee joint prosthesis, the tibial component for a knee joint prosthesis as well as other types of medical implant devices.

The hip joint prosthesis 12 includes a ball head 18 which is sized to fit into a matching acetabular socket 20. The ball head 18 extends from a neck portion 22 which in turn extends from a platform 24 carried by a primary load-bearing member in the form of a stem 26. The stem 26 is operable to be located in a specially reamed cavity 28 in the host femur 16. The stem 26 may be formed of titanium, cobalt chrome, or other suitable materials, and may have various cross-sectional configurations. As will be appreciated by those skilled in the art, the ball head 18 engages the acetabular component 20 which is secured within the pelvis 14.

During the implanting of the hip joint prosthesis 12 into the joint 10 of the patient, the stem 26 and the acetabular component 20 of the hip joint prosthesis 12 are normally anchored in place in part by using bone cement. The cementing of these components generally facilitates the attachment of these components to both the host femur 16 and the pelvis 14. The bone cement is normally formed from a methylmethacrylate monomer and a polymethylmethacrylate polymer. The bone cement is applied to the cavity 28 or to the bony acetabulum which are both prepared to anchor the corresponding components of the hip joint prosthesis 12. The application of the bone cement is normally performed by using a bone cement gun as will be more fully described below.

The present invention provides a bone cement packaging system which allows preparation of the bone cement without exposing the bone cement to the environment. This preparation minimizes the amount of air that may become mixed into the bone cement, minimizes objectionable vapors and further allows the preparation of the bone cement in a low cost package which then can be used to deliver the bone cement into the surgical site with the aid of a bone cement gun.

Referring now to FIGS. 2 through 5, a packaging system for bone cement is shown and is designated generally by the reference numeral 50. The packaging system 50 includes a flexible container 52 and a clamp 54. The flexible container 52 comprises a front panel 56 and a rear panel 58, each made of a thin generally impervious flexible film which is more fully described below. In the embodiment shown in FIGS. 2 through 5, the panels 56 and 58 are each formed from a single sheet of flexible film sealed to each other at a bottom edge 60 and side edges 62 and 64. The flexible container 52 further includes a nozzle 66 which is formed as a flat tubular portion and sealed on its edges 68 similar to the edges 60, 62 and 64.

Figure 4:
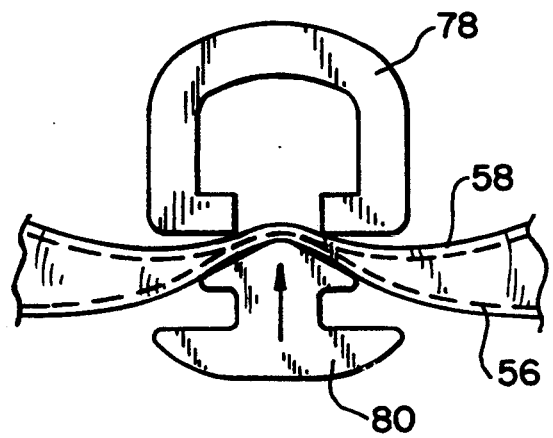
FIG. 4 is a view of the temporary sealing device taken in direction 4—4 in FIG. 3 according to the preferred embodiment of the present invention.

The clamp 54, best shown in FIGS. 3 and 4, is arranged to provide a temporary seal of the inner surfaces of the panels 56 and 58 to each other along a line extending from an initial point 70 on the sealed edge 62 to a terminal point 72 on the sealed edge 64 to form an upper compartment 74 and a lower compartment 76. As will be appreciated by those skilled in the art, the clamp 54 is placed on the flexible container 52 prior to being filled with the polymer component and the monomer component of the bone cement. After the lower compartment 76 is filled with the polymer component, the upper compartment 74 may be filled with the monomer component of the bone cement. The method used for filling the flexible container 52 will be more fully described below.

The clamp 54 comprises a C-shaped outer retention member 78 and an I-shaped inner retention member 80 which partially fits within the hollow of the C-shaped outer retention member 78. When the clamp 54 is assembled with respect to the flexible container 52 as shown in FIG. 4, the outer retention member 78 is positioned on the outside of the rear panel 58 and the inner retention member 80 is positioned on the outside of the front panel 56 such that the panels 56 and 58 are pinched together along a pair of parallel lines extending from the initial point 70 to the terminal point 72. The inner retention member 80 has a contoured upper end which fits within the inner hollow of outer retention member 78 and has a thickness substantially equal to the inner distance between the open ends of the C-shaped section of the outside retention member 78 so that a double thickness of panels 56 and 58 is tightly compressed along a pair of parallel lines to form an effective seal. The outer retention member 78 is made of a resilient material so that the inner retention member 80 may be forced into position therein by placing it over the entire length of the opening of the outer retention member 78 and then pressing it into place. Inner retention member 80 has a contoured upper end which can open the open ends of the C-shaped section of the outside retention member 78 to accommodate the inner retention member 80.

Both the outer retention member 78 and the inner retention member 80 are long enough to reach from the initial point 70 to the terminal point 72. Preferably, inner retention member 80 is somewhat longer than outer retention member 78 to provide for a gripping point when the retention members 78 and 80 are to be separated and removed.

The method of packaging the bone cement within the flexible packaging 52 will now be described. The front panel 56 and rear panel 58 are first formed from a thin generally impervious flexible film. The side edges 62 and 64 of the front panel 56 and the rear panel 58 are then secured to each other by heat sealing. The clamp 54 is then placed between the front panel 56 and the rear panel 58 so as to form a temporary seal between the front panel 56 and the rear panel 58 so as to partially form the upper compartment 74 and the lower compartment 76 under aseptic conditions. The lower compartment 76 is then filled with the polymer component of the bone cement via the open end of the nozzle 66. A seal then closes the lower compartment 76. The flexible container 52 is then gamma irradiated. The monomer component of the bone cement is then filled into the upper compartment 74 under aseptic conditions and then the upper compartment 74 is closed by the seal 60.

Figure 5:
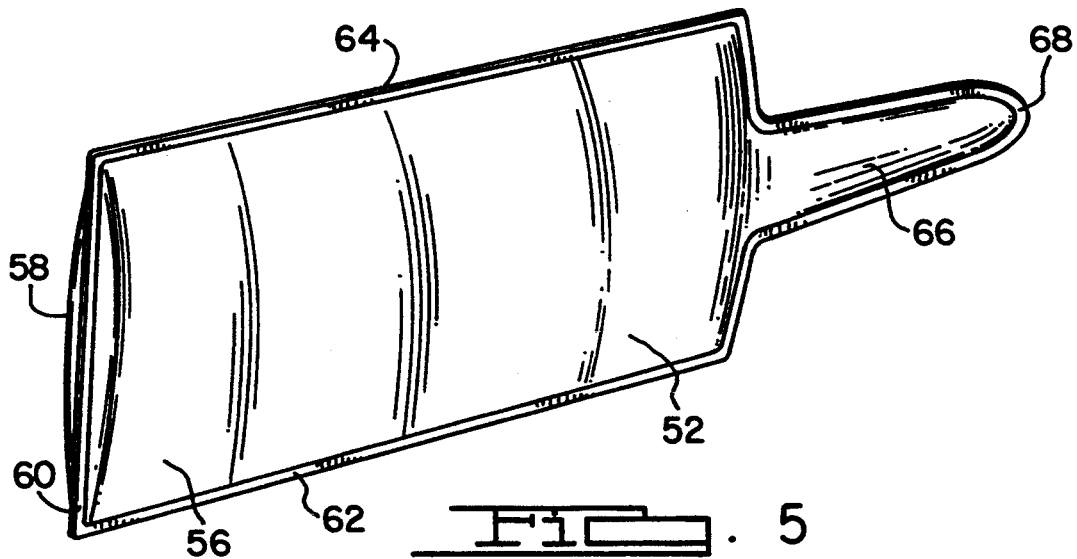
FIG. 5 is a perspective view of the packaging system for bone cement shown in FIG. 2 depicting the packaging system after the temporary sealing device has been removed and the two components of the bone cement are mixed.

When the surgeon decides to use the bone cement within the flexible container 52 and apply the bone cement by hand using the nozzle 66, the inner retention member 80 is separated from the outer retention member 78 to remove the clamp 54 and open the lower compartment 76 to the upper compartment 74 as shown in FIG. 5. The flexible container 52 is then pressed or kneaded so as to mix the individual components of the bone cement. The mixing of the components within the flexible container 52 while the flexible container 52 is intact (i.e., prior to opening) minimizes the inclusion of air and limits the emission of vapors from the components. The flexible container 52 may then be opened by cutting and removing the end of the nozzle 66. Bone cement may then be dispensed by hand by squeezing the flexible container 52.

Figure 6:
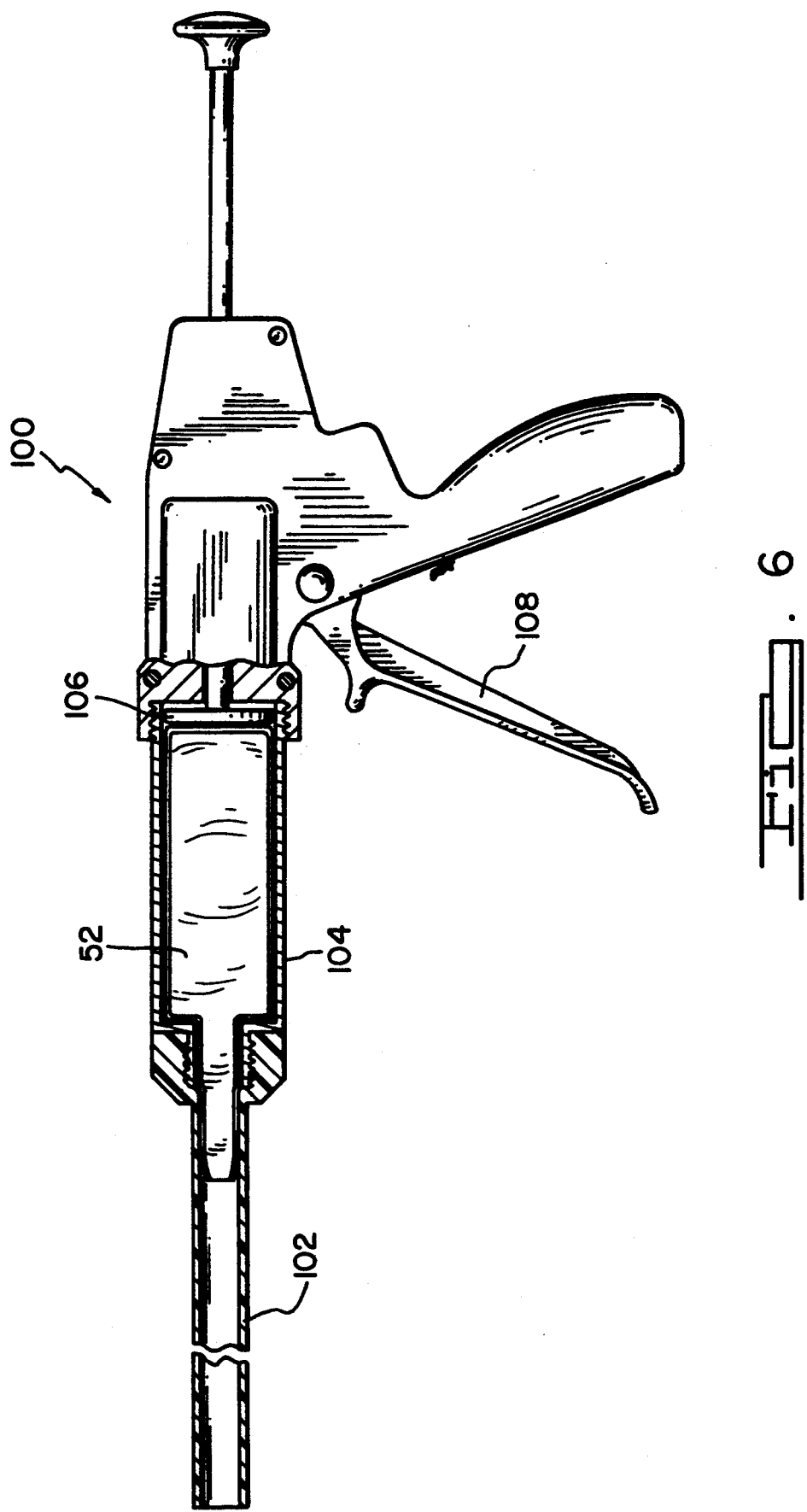
FIG. 6 is a side sectional view of a bone cement gun containing the packaging system for bone cement according to the preferred embodiment of the present invention.
Figure 7:
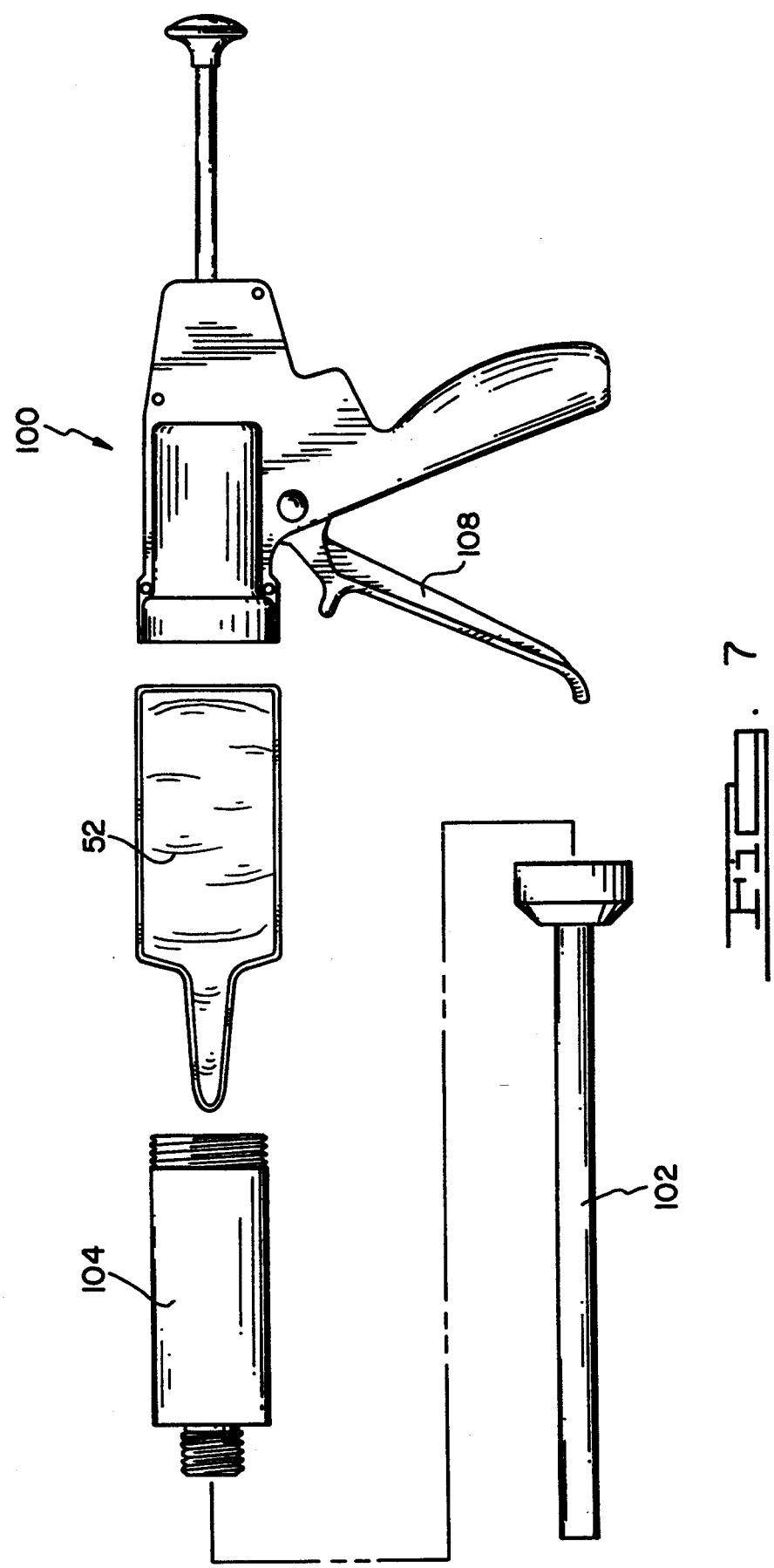
FIG. 7 is an exploded perspective view of the bone cement gun shown in FIG. 6 according to the preferred embodiment of the present invention.

When the surgeon decides to use the bone cement gun 100 as shown in FIGS. 6 and 7, the inner retention member 80 is separated from the outer retention member 78 to remove the clamp 54 and open the lower compartment 76 to the upper compartment 74 as shown in FIG. 5. The flexible container 52 is then pressed or kneaded so as to mix the individual components of the bone cement. The mixing of the components within the flexible container 52 also minimizes the inclusion of air and minimizes emitted vapors. Once mixing is complete, the flexible container 52 is inserted into a bone cement syringe 104 and then the nozzle 66 is opened. After the bone cement syringe 104 is inserted into the bone cement gun 100, a tubular member 102 is then secured to the open end of the bone cement syringe 104 with the nozzle 66 of the flexible container 52 extending into the tubular member 102 as shown in FIG. 6. An actuation mechanism 108 is then squeezed which in turn moves a plunger 106 to the left as shown in FIG. 6 forcing the bone cement out of the flexible container 52 through the tubular member 102. Once the bone cement has been pumped from the bone cement gun 100, the flexible container 52 can be removed from the bone cement syringe 104 leaving a clean bone cement gun 100 and bone cement syringe 104 which then can be reused for dispensing additional quantities of bone cement.

The nature of the thin generally impervious flexible film to be used with the flexible container 52 of the present invention depends upon the nature of the materials to be stored and the conditions under which the materials will be mixed and used. For many materials, polyethylene film is suitable. Other suitable films include mylar, teflon, and various combinations of the foregoing materials. However, it will be appreciated that other suitable materials may also be used. Generally, thermoplastic films are used and the seals 60, 62, 64 and 68 are heat seals. However, thermoplastic films are not essential and seals 60, 62, 64 and 68 may be adhesive seals.

The nature of the clamp 54 may also vary. The clamp 54 described in connection with the present invention consisting of an I-shaped inner retention member 80 and a C-shaped outer retention member 78 is preferred because of its simplicity and ease of handling. However, other types of clamps suitable for applying pressure to the flexible container 52 may also be used. In addition, it is possible to replace the clamp 54 with an additional separation seal (not shown). In this embodiment, the separation seal can be either a heat seal or an adhesive seal to separate the upper compartment 74 from the lower compartment 76. The strength of this separation seal must be such that it can be broken by placing pressure on either of the compartments 74 and 76 without damaging the panels 56 and 58. This separation seal may also be used in conjunction with the clamp 54.

It will also be appreciated that the flexible container 52 need not be made from separate sheets of film sealed at their bottom edge 60 as shown in FIGS. 2 through 5. The flexible container 52 may be made from a double sized flexible sheet of film folded at the bottom edge 60 thereby providing a folded edge to seal the bottom of flexible container 52. In another embodiment, the flexible container 52 may be made from a segment of a film sleeve, in which case edges 62 and 64 would be folded edges while bottom edge 60 would be a sealed edge.

Figure 8:
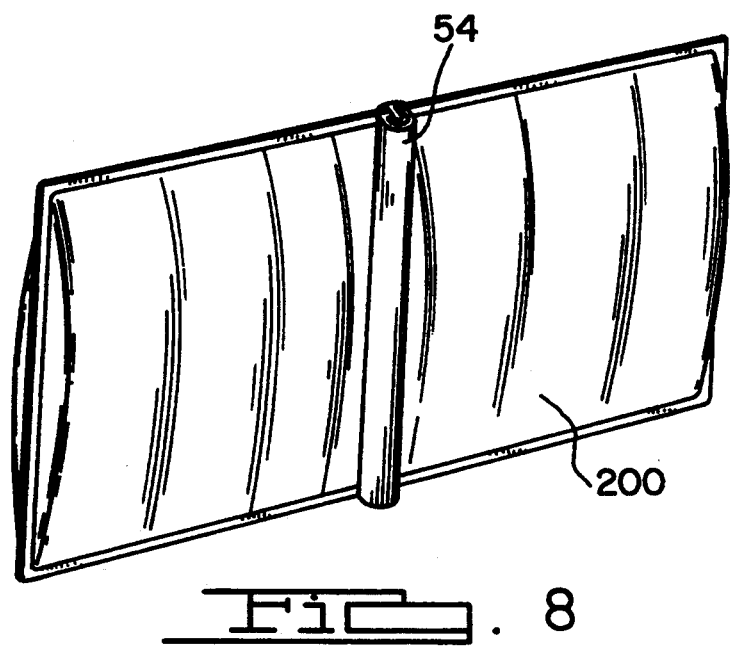
FIG. 8 is a perspective view of the packaging system for bone cement in accordance with another preferred embodiment of the present invention.

While the present invention has been described with respect to a flexible container 52 which is essentially rectangular in shape having a nozzle, it is to be understood that the present invention is applicable to flexible containers of other shapes, such as rectangular, triangular or trapezoid bags, or flexible containers having curved edges. FIG. 8 shows a perspective view of a rectangular flexible container 200 which does not have the nozzle 66. In this embodiment, after removal of the clamp 54 and the mixing of the two components of bone cement, the end of the rectangular flexible container 200 can be removed and the bone cement can be dispensed from the flexible container 200 by hand or by a roller (not shown). The surgeon can then place the bone cement within the appropriate bone cavity by using any type of an applicator. In addition, the location of the clamp 54 need not be along a midline as shown in the figures, but may be closer to the bottom edge or the top edge to provide compartments of different sizes if the nature of the final composition of the bone cement requires different amounts of each compartment. In addition, the clamp 54 may be disposed lengthwise on the flexible container 52 rather than longitudinally. Furthermore, various other types of nozzles may be attached to the bone cement syringe to accommodate the needs of the surgeon. Finally, the components of the bone cement may be vacuum packaged within the flexible container.

While the above detailed description describes the preferred embodiment of the present invention, it should be understood that the present invention is susceptible to modification, variation and alteration without deviating from the scope and fair meaning of the subjoined claims.

What is claimed is:

1. An apparatus for dispensing bone cement wherein said bone cement is formed by mixing at least a first component with a second component, said apparatus comprising:

a flexible container being operable to store said first and second components, said flexible container including:
   (a) a first compartment being operable to store said first component of said bone cement,
   (b) a second compartment being operable to store said second component of said bone cement;

means for temporarily separating said first compartment and said second compartment wherein removal of said means for temporarily separating said first compartment and said second compartment from said flexible container permits said first and second components to be mixed so as to form said bone cement;

means for supporting said flexible container within said apparatus; and means for causing said flexible container to dispense said bone cement from said apparatus.

2. The apparatus according to claim 1 wherein said second component of said bone cement is stored in said second compartment under a vacuum.

3. The apparatus according to claim 1, wherein said means for temporarily separating said first compartment and said second compartment comprises a heat seal disposed between said first and second compartments.

4. The apparatus according to claim 1, wherein said means for temporarily separating said first compartment and said second compartment comprises an adhesive seal disposed between said first and second compartments.

5. The apparatus according to claim 1, wherein said means for temporarily separating said first compartment and said second compartment comprises:
   (a) an outer retention member; and
   (b) an inner retention member adapted to be received by said outer retention member;
said outer retention member and said inner retention member being operable to engage said flexible container therebetween.

6. The apparatus according to claim 1, further comprising a nozzle being in communication with said first compartment.

7. The apparatus according to claim 6, wherein said means for temporarily separating said first compartment and said second compartment comprises:
an elongated C-shaped outer retention member; and
an elongated I-shaped inner retention member adapted to be received by said elongated C-shaped outer retention member.

8. The apparatus according to claim 7, wherein said first and second compartments are formed in part by a first panel of a generally flexible film.

9. A method of preparing and applying bone cement which is formed by mixing at least a first component and second component, said method comprising the steps of:
   disposing said first and second components in a flexible package having at least a first compartment and a second compartment, said first compartment being operable to store said first component and said second compartment being operable to store said second component, said first and second compartments being separated by a temporary seal;
   removing said temporary seal thereby allowing said first and second components to mix Within said flexible package so as to form said bone cement;
   inserting said flexible package into a bone cement gun; and
   operating said bone cement gun so as to cause said bone cement to be dispensed from said flexible package.

10. The method according to claim 9 wherein said step of disposing said first and second components in a flexible package includes the step of drawing a vacuum within said first compartment.

11. The method of claim 9, wherein said step of disposing said first and second components in a flexible package includes the steps of:
   providing a first panel made of a generally flexible film;
   providing a second panel made of a generally flexible film;
   partially sealing said first panel to said second panel so as to partially form said flexible package;
   forming a temporary seal between said first panel and said second panel so as to partially form said first compartment and partially form said second compartment;
   filling said flexible package with said first component of said bone cement;
   filling said second compartment with said second component of said bone cement; and
   sealing the remainder of said first panel to said second panel so as to completely form said flexible package.

12. The method according to claim 11, wherein said step of forming a temporary seal between said first panel and said second panel includes the step of heat sealing said first panel to said second panel.

13. The method according to claim 11, wherein said step of forming a temporary seal between said first panel and said second panel includes the step of adhesively bonding said first panel to said second panel.

14. The method according to claim 11, wherein said step of forming a temporary seal between said first panel and said second panel includes the step of pinching said first and second panels between an elongated C-shaped outer retention member and an elongated I-shaped inner retention member, said I-shaped inner retention member being adapted to be received by said C-shaped outer retention member.

15. The method according to claim 9, wherein said step of removing said temporary seal thereby allowing said first and second component to mix includes the step of limiting the emission of vapors from said first and second components while said first and second components are being mixed.

16. The method according to claim 15, wherein said step of removing said temporary seal thereby allowing said first and second components to mix includes the step of mixing said first and second components while said flexible package is intact.

17. The method according to claim 9 wherein said step of disposing said first and second components in a flexible package includes the step of drawing a vacuum within said second compartment.

18. A method of packaging bone cement formed from at least a first component and a second component, said method comprising the steps of:
   providing a first panel formed from a generally flexible film;
   providing a second panel formed from a generally flexible film;
   partially sealing said first panel to said second panel to partially form a flexible package;
   forming a temporary seal between said first panel and said second panel to form a first compartment and partially form a second compartment, said first compartment containing said first component of said bone cement, said step of forming a temporary seal including pinching said first and second panel between an elongated C-shaped outer retention member and an elongated I-shaped inner retention member, said I-shaped inner retention member being adapted to be received by said C-shaped outer retention member;
   filling said flexible package with said first component of said bone cement;
   filling said second compartment with said second component of said bone cement;
   sealing the remainder of said first panel to said second panel so as to completely form said flexible container.

19. The method according to claim 18, wherein said step of forming a temporary seal between said first panel and said second panel includes the step of adhesively bonding said first panel to said second panel.

20. The method according to claim 18, wherein said step of forming a temporary seal between said first panel and said second panel includes the step of pinching said first and second panels between an elongated C-shaped outer retention member and an elongated I-shaped inner retention member, said I-shaped inner retention member being adapted to be received by said C-shaped outer retention member.

21. The method according to claim 18, wherein the step of forming a temporary seal between said first panel and said second panel includes the step of heat sealing said first panel to said second panel.

22. The method according to claim 18 further comprising the step of drawing a vacuum within said first compartment.

23. The method according to claim 18 further comprising the step of drawing a vacuum within said second compartment.

24. An apparatus for dispensing bone cement wherein said bone cement is formed by mixing at least a first component with a second component, said apparatus comprising:
 a flexible container being operable to store said first and second components, said flexible container including:
  (a) a first compartment being operable to store said first component of said bone cement, said first component being stored in said first compartment under a vacuum,
  (b) a second compartment being operable to store said second component of said bone cement;
  (c) means for temporarily separating said first compartment and said second compartment wherein removal of said means for temporarily separating said first compartment and said second compartment from said flexible container permits said first and second components to be mixed so as to form said bone cement;
 means for supporting said flexible container within said apparatus; and
 means for causing said flexible container to dispense said bone cement from said apparatus.

25. A method of preparing and applying bone cement which is formed by mixing at least a first component and a second component, said method comprising the steps of:
 disposing said first component in a flexible package having at least a first compartment and a second compartment, said first compartment being operable to store said first component and said second compartment being operable to store said second component, said first and second compartments being separated by a temporary seal;
 drawing a vacuum within said first compartment of said flexible container so as to place said first component under a vacuum;
 disposing said second component in said second compartment of said flexible package;
 removing said temporary seal thereby allowing said first and second components to mix within said flexible package so as to form said bone cement; and
 applying said bone cement after said first and said second components have been mixed.

26. A method of packaging bone cement formed from at least a first component and a second component, said method comprising the steps of:
 providing a first panel formed from a generally flexible film;
 providing a second panel formed from a generally flexible film;
 partially sealing said first panel to said second panel to form a flexible package;
 forming a temporary seal between said first panel and said second panel to form a first compartment and partially form a second compartment, said first compartment being operable to contain said first component of said bone cement and said second compartment being operable to contain said second component of said bone cement;
 drawing a vacuum in at least one of said first and second compartments; and
 sealing the remainder of said first panel to said second panel so as to completely form said flexible container.

* * * * *